United States Patent [19]

Nadeau et al.

[11] Patent Number: 4,811,605

[45] Date of Patent: Mar. 14, 1989

[54] APPARATUS AND METHOD FOR INSPECTING THE DEGRADATION OF A GAS NOZZLE

[75] Inventors: Francois Nadeau, St-Bruno; Michael T. Braeuel, St-Lambert, both of Canada

[73] Assignee: Canadian Patents and Development Limited/Societe Canadienne des Brevets et D'Exploitation Limitee, Ottawa, Canada

[21] Appl. No.: 162,071

[22] Filed: Feb. 29, 1988

[51] Int. Cl.[4] ............................................. G01N 29/00
[52] U.S. Cl. ......................................... 73/645; 73/583
[58] Field of Search ................. 73/584, 587, 592, 645, 73/646, 582, 579, 168, 583, 659; 239/71

[56] References Cited

U.S. PATENT DOCUMENTS

| 2,541,164 | 2/1951 | Huenlich | 181/18 |
| 3,556,120 | 1/1971 | Bauer | 137/81.5 |
| 3,924,456 | 12/1975 | Vahaviolos | 73/587 |
| 3,985,024 | 10/1976 | Horak | 73/71.4 |
| 4,009,463 | 2/1977 | Vercellotti et al. | 340/16 R |
| 4,033,179 | 7/1977 | Romrell | 73/71.4 |
| 4,090,400 | 5/1978 | Vahaviolos | 73/582 |
| 4,117,733 | 10/1978 | Gugel | 73/634 |
| 4,435,631 | 3/1984 | Drouet et al. | 219/124.02 |
| 4,472,971 | 9/1984 | Marini et al. | 73/587 |

FOREIGN PATENT DOCUMENTS

| 1100222 | 4/1981 | Canada . | |
| 206853 | 2/1925 | United Kingdom | 73/646 |
| 1430824 | 4/1976 | United Kingdom . | |

OTHER PUBLICATIONS

Acoustic Emission: Another Tool for the Materials Analyst, S. B. Bellosillo, Canadian Research & Development, May–Jun. 1972, pp. 23–28.

Recent Developments in Ultrasonics, H. W. Meyfarth, The Professional Engineer and Engineering Digest, Oct. 1966, pp. 43–47.

Primary Examiner—Stewart J. Levy
Assistant Examiner—Louis M. Arana
Attorney, Agent, or Firm—Foley & Lardner, Schwartz, Jeffery, Schwaab, Mack, Blumenthal & Evans

[57] ABSTRACT

The present disclosure describes an apparatus and a method for inspecting the degradation of a gas nozzle. The nozzle is of the type that can produce a whistle when a gas is blown through the nozzle. The method comprises the steps of detecting an acoustic signal emitted by the nozzle when the gas is blown through the nozzle, the gas having a pressure selected to produce an acoustic resonance at a certain frequency; generating an electrical signal responsive to the detected acoustic signal; band pass filtering the electrical signal at the frequency; and detecting the amplitude of the electrical signal at the frequency. The method also comprises the steps of comparing the amplitude of the electrical signal with a reference amplitude corresponding to a reference nozzle; and displaying a signal indicative of the degradation of the nozzle according to the signal resulting from the comparing step.

11 Claims, 4 Drawing Sheets

APPARATUS AND METHOD FOR INSPECTING THE DEGRADATION OF A GAS NOZZLE

BACKGROUND OF THE INVENTION

1. Field of the invention

The present invention relates generally to an apparatus and a method for inspecting the degradation of a gas nozzle. The nozzle is of the type that can produce a whistle when a gas is blown through the nozzle.

2. Description of the prior art

In recent years, the plasma arc cutting process has gained wide acceptance as a cost-effective means of cutting steel, aluminium, and stainless steel. The process was invented in 1955 and was originally intended for cutting aluminium, although approximately 80 percent of plasma arc cutting is now used for cutting carbon steel below ½ inch thick. Many of today's plasma arc cutting systems are highly automated workcells that can be integrated into a CAD-CAM environment. Like other cutting process, plasma arc cutting works by locally applying heat and momentum on the workpiece to melt it and expel the molten material. A cutting gas, such as nitrogen, flowing out of a nozzle at high velocity provides the momentum while an electric arc, burning through the same nozzle between a tungsten electrode and the workpiece, provides the heat. This arc is called a "transferred arc" because it is sprung from a pilot arc initially struck between the electrode and the nozzle.

The orifice of the nozzle must sustain the high-velocity flow of the cutting gas, which is heated to a plasma of more than 30,000° C. Thus the nozzle is a very critical component of any plasma arc cutting system because it tends to wear rapidly under such extreme operating conditions, and the resulting change in the geometry of the orifice affects the hydrodynamic behavior of the plasma jet, which consequently degrades the quality of the cut.

It is known that tip life is very dependent on operating conditions such as torch stand-off, cutting gas mixture, and current density. The following conditions and their causes are examples of nozzle defects: general wear, which consists of axisymetric erosion of the orifice and occurs after prolonged use and usually on the exit edge; pitting, a chipping of portions of the inner orifice caused by too-low-cutting gas flow, gas contamination, loss of gas swirl, a swirl being forced on the gas flow to reduce nozzle wear, or excessive striking of the pilot arc; blow out, an extended case of pitting caused by overpowering which consists of a too high current density for the nozzle; blowback, which usually occurs during piercing when cut material is blown back up the tip; and calcium build up which is a problem associated with water-injection plasma cutting.

The detection of these conditions is currently performed visually, either through direct inspection of the tip or indirectly when a deterioration of cut quality or unreliable arc initiation is observed. No sensing technique that could replace human intervention exists or has been reported. This is a problem, particularly with large automated plasma arc cutting systems, where a faulty tip can cause substantial waste of time and material due to bad cuts.

SUMMARY OF THE INVENTION

One of the objects of the present invention is to automate the inspection of a gas nozzle.

Another object of the present invention is to provide a more reliable inspection of a gas nozzle.

According to the present invention, there is provided a method for inspecting the degradation of a gas nozzle, said nozzle being of the type that can produce a whistle when a gas is blown through said nozzle, comprising the steps of:

(a) detecting an acoustic signal emitted by said nozzle when said gas is blown through said nozzle, said gas having a pressure selected to produce an acoustic resonance at a certain frequency;

(b) generating an electrical signal responsive to said acoustic signal detected in said step (a);

(c) band pass filtering said electrical signal at said frequency;

(d) detecting the amplitude of said electrical signal at said frequency;

(e) comparing the amplitude of said electrical signal with a reference amplitude corresponding to a reference nozzle; and (f) displaying a signal indicative of the degradation of said nozzle according to the signal resulting from said comparing step (e).

According to the present invention, there is also provided an apparatus for inspecting the degradation of a gas nozzle, said nozzle being of the type that can produce a whistle when a gas is blown through said nozzle, comprising:

electroacoustic means for detecting an acoustic signal emitted by said nozzle when said gas is blown through said nozzle, and generating an electrical signal responsive to said acoustic signal, said gas having a pressure selected to produce an acoustic resonance at a certain frequency;

filtering means for band pass filtering said electrical signal at said frequency;

detecting means for detecting the amplitude of said electrical signal at said frequency;

comparing means for comparing the amplitude of said electrical signal with a reference amplitude corresponding to a reference nozzle; and display means for displaying a signal indicative of the degradation of said nozzle according to the output of said comparing means.

Other forms, features and advantages of the invention will appear from the description of preferred embodiments that follows, having reference to the appended drawings.

DESCRIPTION OF THE DRAWINGS

There is a special group of jet acoustic problems referred to as jet edge systems, i.e., edge tones, hole, and ring tones. For certain ranges of Reynolds numbers, jet edge systems become hydrodynamic oscillators controlled by acoustic feedback. The whistling teapot is a common example of such a system. A ring vortex forms at the leading edge of the nozzle, travels through the orifice at about 74 percent of &he local shear layer velocity, and is finally shed into open space, generating an acoustic impulse that triggers the formation of another vortex. This periodic shedding of vortices produces a harmonic sound or whistle in which the fundamental frequency is proportional to the flow velocity. For a given orifice, one can define a dimensionless number called the Strouhal number:

$$st = (f \cdot D)/(v)$$

where
st Strouhal number,
f shedding frequency,
v mean flow velocity,
D characteristic length such as orifice diameter or orifice length.

An essential condition to ring vortex formation is the separation of flow by a sharp and even leading edge, creating an axisymetrical boundary layer in which nascent vortices develop. Rounding or nicking of the inlet edge can disrupt vortex formation and consequently make the whistle disappear.

Figure 1:
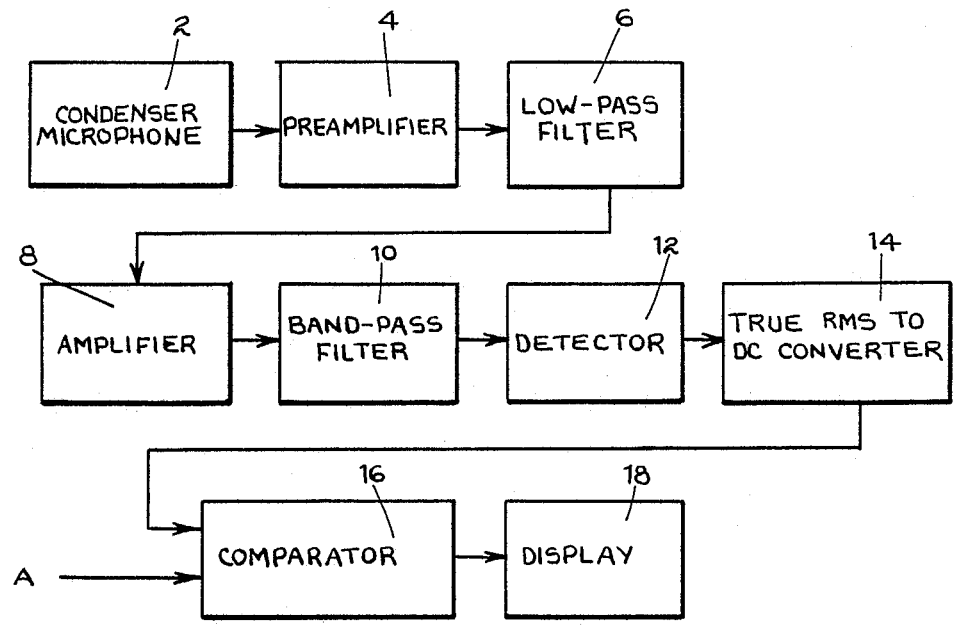
FIG. 1 is a bloc diagram illustrating one embodiment of the present invention.

Referring now to FIG. 1, there is shown an apparatus for inspecting the degradation of a gas nozzle (not shown). The apparatus comprises a condenser microphone 2 for detecting an acoustic signal emitted by the nozzle when the gas is blown through the nozzle. The condenser microphone 2 generates an electrical signal responsive to the detected acoustic signal. The gas has a pressure selected to produce an acoustic resonance at a certain frequency. The signal is processed by a preamplifier 4, a low-pass filter 6 and an amplifier 8. The output of the amplifier 8 is processed by a band pass filter 10 adjusted at the frequency of the acoustic resonance. The amplitude of the signal at this frequency is detected by a detector 12. The output of the detector is converted into a DC signal by a true RMS to DC converter 14.

Then, the output of the converter 14 is compared with a reference amplitude corresponding to a reference nozzle by means of a comparator 16. The reference amplitude is introduced at A. A display 18 is provided for displaying a signal indicative of the degradation of the nozzle according to the output of the comparator 16. The specifications of the band-pass filter 10 are $\omega_c = 16.4$ kHz, $Q=12$ and a gain of 10.

In operation, an acoustic signal emitted by the nozzle when a gas is blown through the nozzle is detected by the condenser microphone 2, and a signal responsive to the detected acoustic signal is generated. The electrical signal is then band-pass filtered at the resonant frequency, and the amplitude of this filtered electrical signal is detected. The amplitude of the detected electrical signal is compared with a reference amplitude corresponding to a reference nozzle, and a signal is displayed to indicate the degradation of the nozzle according to the signal resulting from the comparing.

The reference amplitude may correspond to the amplitude of an acoustic resonance emitted from an undegraded new nozzle. Then, the signal resulting from the comparing step may be a value in percentage representative of the detected amplitude compared with the reference amplitude which represents a value of 100%.

In another embodiment, the reference amplitude may correspond to a percentage of the amplitude of the acoustic resonance emitted from an undegraded new nozzle. Then the detected amplitude is compared with this reference amplitude. If the detected amplitude is higher or equal to the reference amplitude then the degradation of the nozzle is considered acceptable. If not, then the degradation of the nozzle is considered unacceptable. The reference amplitude in this latter case may correspond to a percentage of 75% of the amplitude of the acoustic resonance emitted from the undegraded new nozzle.

It has been found that good results are obtained when the length of the nozzle is 0.5 to 2 times the diameter of the aperture of the nozzle. The operating pressure of the nozzle may be chosen so that the amplitude of the acoustic resonance is maximum to obtain an optimum signal to noise ratio.

It has been found that good results are obtained when the flow of gas through the nozzle is characterized by a Reynolds number having a value from $5 \times 10^3$ to $20 \times 10^3$.

Figure 2:
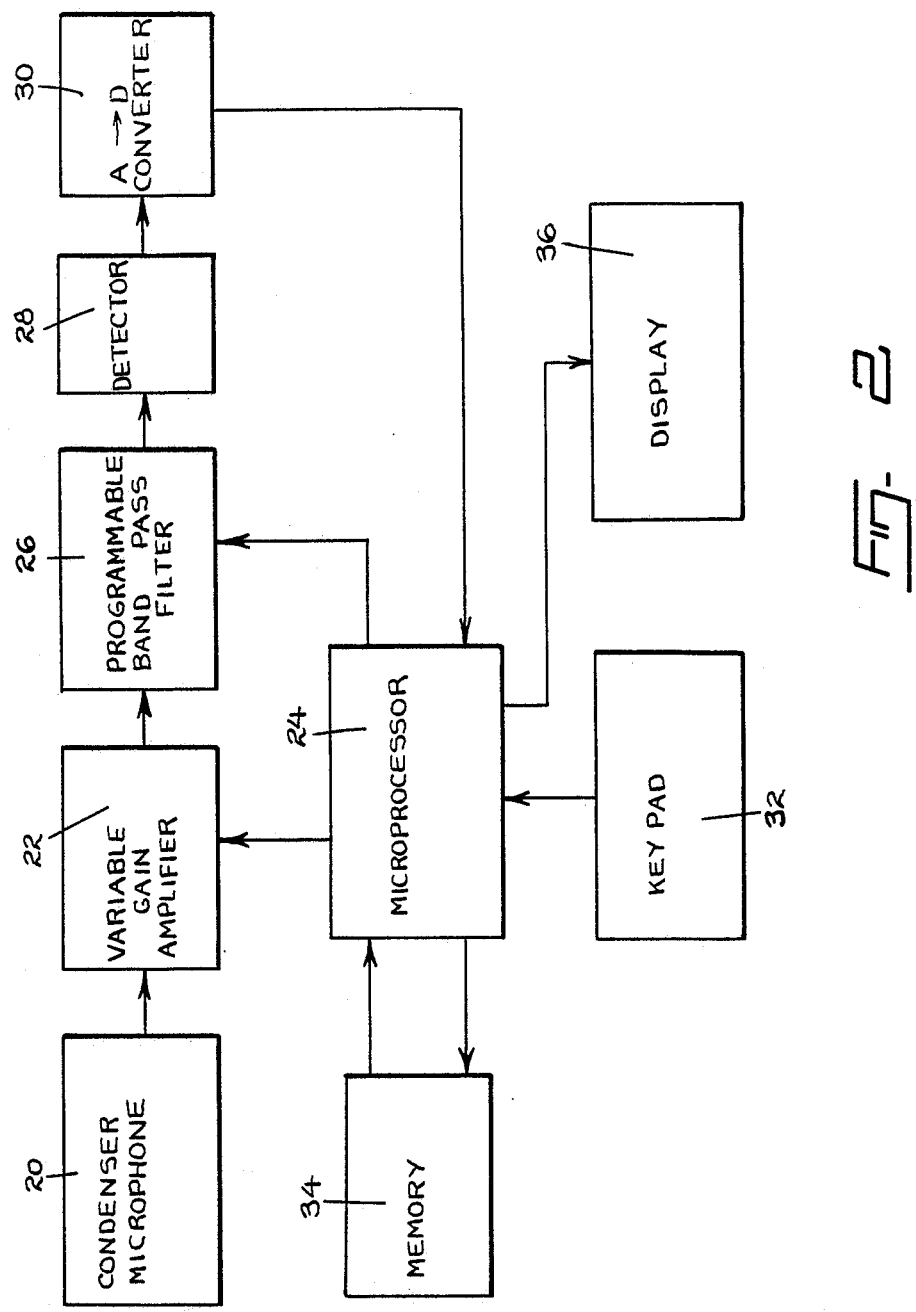
FIG. 2 is another bloc diagram illustrating another embodiment of the present invention.

Referring now to FIG. 2, there is shown another embodiment of the present invention. This apparatus also comprises a condenser microphone 20 for detecting the acoustic signal emitted by the nozzle, and generating an electrical signal accordingly. A variable gain amplifier 22 is provided to amplify the output of the condenser microphone 20. The gain of the variable gain amplifier 22 is controlled by a microprocessor 24. The output of the amplifier 22 is processed by a programmable band pass filter 26. The filtering frequencies of the band pass filter 26 are also controlled by the microprocessor 24 so that, in a calibration mode, the programmable band pass filter 26 can scan the spectrum of the output signal of the amplifier 22 to locate the frequency corresponding to a resonance.

The output of the programmable band pass filter 26 is connected to a detector 28 for measuring the amplitude of the signal filtered by the band pass filter 26. The output of the detector 28 is processed by an analog to digital converter 30 and sent to the microprocessor 24. The microprocessor 24 is provided with a key pad 32 permitting to a user to choose the operation mode of the apparatus. The microprocessor 24 is provided with a memory 34 that memorizes data obtained during the calibration mode.

The apparatus is also provided with a display 36 that gives to the user a signal indicative of the degradation of the nozzle under test.

This apparatus can perform in an inspecting mode or a calibration mode. Before operating the apparatus in the inspecting mode, the user must perform a calibration mode. In the calibration mode, the acoustic sound emitted by a new undegraded nozzle is detected by the condenser microphone 20. The output of the microphone is amplified by the variable gain amplifier 22 at its maximum gain. The spectrum of the output of the amplifier 22 is scanned by the programmable band pass filter 26 to locate the frequency corresponding to a resonance. The amplitude of the filtered signal is detected and converted into digital form, and sent to the microprocessor 24. If during the scanning, a saturated signal is detected, then the gain of the amplifier 22 is divided by two till the saturation in the detected signal is eliminated. Information characterizing the gain of the amplifier 22 is kept in the memory 34. The microprocessor 24 also stores in memory the value of the maximum amplitude detected during the scanning, and the frequency at which this resonance occurs. When the calibration operation is completed, the apparatus is ready to perform in the inspecting mode.

The data kept in memory will be used in the inspecting mode to set the gain of the variable gain amplifier, the filtering frequency of the band pass filter, and the value of the reference amplitude.

Figure 3:
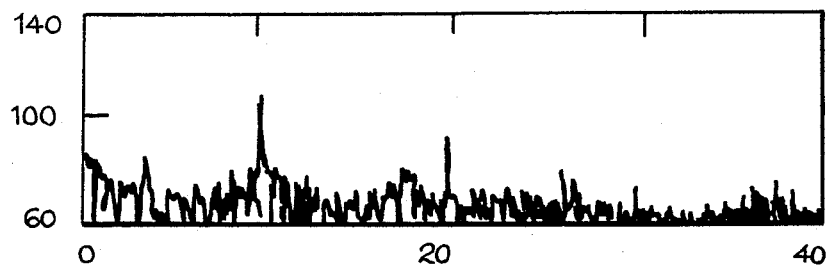
FIGS. 3, 4 and 5 are diagrams illustrating spectrums of sound produced by flow of gas through a nozzle, the flow in these figures being characterized by different Reynolds numbers.
Figure 4:
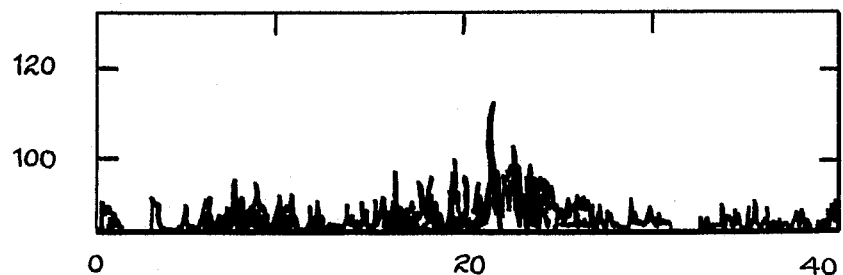
Figure 5:
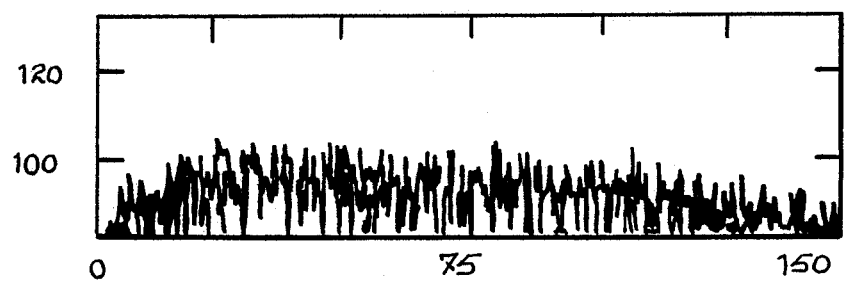

Referring now to FIGS. 3, 4 and 5, there is shown the effect of increasing Reynolds number in the spectrum of sound produced by flow of cutting gas through a 0.287 cm diameter nozzle. The vertical axes represent the amplitude in DB, and the horizontal axes represent the frequency in kHz.

The sound produced by the flow of the cutting gas through the nozzle with no cutting arc ignited was measured for various gas flows. The experimental setup consisted essentially of a plasma arc cutting machine, sound measurement instrumentation, and a data acquisition system. The microphone was aimed at the nozzle output and located on a plane perpendicular to the torch axis at a distance r of 8 to 15 cm away. This region was in the far field of the source as indicated by an observed 1/r decay of amplitude. The cutting equipment from Thermal Dynamics (Trade Mark) comprises a power source and a torch. The shape of the orifice was a sharp-edged cylindrical hole.

The acoustic signal was recorded by a numeric oscilloscope and the digitized waveforms were transfered to a computer for spectral analysis. FIGS. 3, 4 and 5 have respectively a flow rate characterized by Reynolds numbers equal to $9.1 \times 10^3$, $1.7 \times 10^4$ and $6.9 \times 10^4$. These figures show the evolution of the sound spectrum as the gas flow increases for the torch with a D=0.287 cm nozzle. We observe at lower flow rates, i.e., lower Reynolds numbers, the presence of sharp and harmonically spaced peaks indicating the gas flow through the nozzle is generating a periodic but non-sinusoidal pressure variation. As the flow rate increases, so does the frequency of this whistling. The broadband noise also rises and eventually buries the tonal peaks.

FIG. 3 depicts a typical spectrum of a resonating nozzle showing the fondamental at 10 kHz with evenly spaced and highly attenuated harmonics.

The FIG. 4 represents a spectrum corresponding to a Reynolds number approximately twice that of the FIG. 3, a proportional shift in the fundamental frequency occurs. The frequency components adjacent to the resonance begin to merge into the resonant frequency. This merging effect continues until no apparent feature exists, as illustrated in the FIG. 5 corresponding to a Reynolds number of $6.9 \times 10^4$ based on an extrapolated bulk mean velocity.

Figure 6:
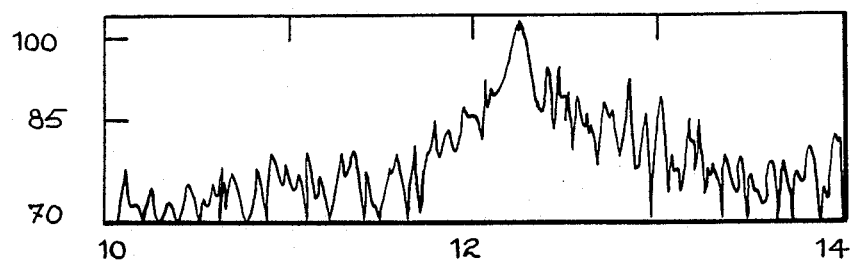
FIG. 6 is a diagram illustrating a spectrum of sound produced by flow of gas through a new nozzle.
Figure 7:
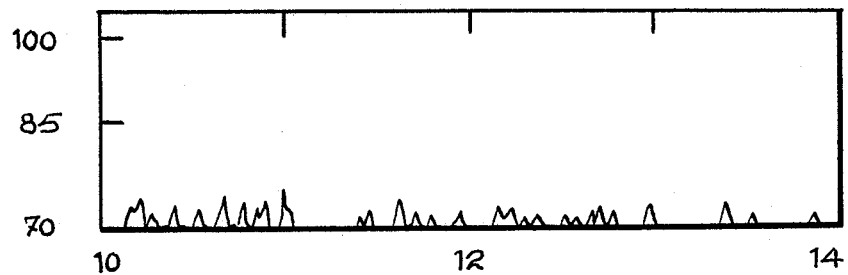
FIGS. 7 and 8 are diagrams illustrating spectrums of sound produced by flow of gas through different damaged nozzles.
Figure 8:
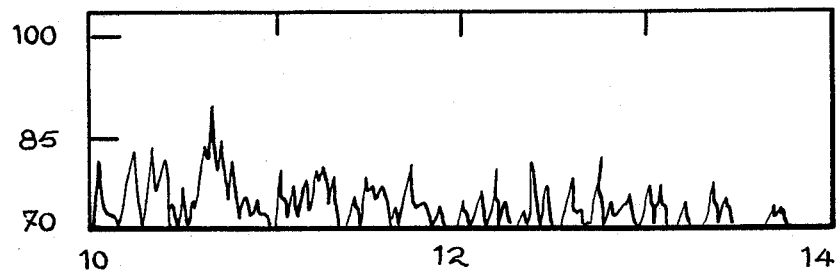

Referring now to FIGS. 6, 7 and 8, there are shown detailed spectra of resonance showing effect of various type of defects. The vertical axes represent the amplitude in DB, and the horizontal axes represent the frequency in kHz.

FIG. 6 illustrates the spectrum of an unused new nozzle. The amplitude and the frequency of the resonance can be easily seen from this figure.

FIG. 8 illustrates the spectrum of a nozzle damaged by a small pit. Such small pit is barely visible but produces an important reduction in the amplitude of the resonance along with a moderated frequency shift.

FIG. 7 illustrates the spectrum of a nozzle severely damaged. The amplitude of the resonance disappears completely.

The embodiments of the invention in which an exclusive property of privilege is claimed are defined as follows:

1. A method for inspecting the degradation of a gas nozzle, said nozzle being of the type that can produce a whistle when a gas is blown through said nozzle, comprising the steps of:
   (a) detecting an acoustic signal emitted by said nozzle when said gas is blown through said nozzle, said gas having a pressure selected to produce an acoustic resonance at a certain frequency;
   (b) generating an electrical signal responsive to said acoustic signal detected in said step (a);
   (c) band pass filtering said electrical signal at said frequency;
   (d) detecting the amplitude of said electrical signal at said frequency;
   (e) comparing the amplitude of said electrical signal with a reference amplitude corresponding to a reference nozzle; and
   (f) displaying a signal indicative of the degradation of said nozzle according to the signal resulting from said comparing step (e).

2. A method according to claim 1, wherein said reference amplitude corresponds to the amplitude of an acoustic resonance emitted from an undegraded new nozzle, and wherein the signal resulting from step (e) is a value in percentage representative of the amplitude detected in step (d) compared with said reference amplitude which represents a value of 100%.

3. A method according to claim 1, wherein said reference amplitude corresponds to a percentage of the amplitude of an acoustic resonance emitted from an undegraded new nozzle, and wherein the signal resulting from step (e) is a value representative of the comparing of said amplitude detected in step (d) with said reference amplitude so that if said detected amplitude is higher or equal to said reference amplitude then the degradation of said nozzle is considered acceptable, if not then the degradation of said nozzle is considered unacceptable.

4. A method according to claim 3, wherein said reference amplitude corresponds to a percentage of 75% of the amplitude of said acoustic resonance emitted from an undegraded new nozzle.

5. A method according to claim 1, wherein said nozzle has a length which is 0.5 to 2 times the diameter of the aperture of said nozzle.

6. A method according to claim 1, wherein the flow of gas through said nozzle is characterized by a Reynolds number having a value from $5 \times 10^3$ to $20 \times 10^3$.

7. A method according to claim 1, wherein said pressure is chosen so that the amplitude of said acoustic resonance is maximum to obtain an optimum signal to noise ratio.

8. A method according to claim 1, wherein said reference amplitude is established by the following steps:
   (i) detecting an acoustic sound emitted by a new undegraded nozzle when a gas is blown through said new nozzle, said gas having a pressure selected to produce said acoustic resonance at said frequency;

(ii) generating an electrical signal responsive to said acoustic signal detected in said step (i);

(iii) scanning the spectrum of said electrical signal generated in said step (ii) to locate said frequency corresponding to said resonance;

(iv) measuring the amplitude of said acoustic resonance at said frequency to obtain said reference amplitude; and (v) storing said amplitude measured in said step (iv) and a value representative of said frequency in a memory.

9. An apparatus for inspecting the degradation of a gas nozzle, said nozzle being of the type that can produce a whistle when a gas is blown through said nozzle, comprising:

electroacoustic means for detecting an acoustic signal emitted by said nozzle when said gas is blown through said nozzle, and generating an electrical signal responsive to said acoustic signal, said gas having a pressure selected to produce an acoustic resonance at a certain frequency;

filtering means for band pass filtering said electrical signal at said frequency;

detecting means for detecting the amplitude of said electrical signal at said frequency;

comparing means for comparing the amplitude of said electrical signal with a reference amplitude corresponding to a reference nozzle; and display means for displaying a signal indicative of the degradation of said nozzle according to the output of said comparing means.

10. An apparatus according to claim 9, wherein said nozzle has a length which is 0.5 to 2 times the diameter of the aperture of said nozzle.

11. An apparatus according to claim 9, comprising a calibration means having:

scanning means for scanning the spectrum of an electrical signal generated by said electroacoustic means, when a gas is blown through a new undegraded nozzle, to locate said frequency corresponding to said resonance;

measuring means for measuring the amplitude of said acoustic resonance at said frequency to obtain said reference amplitude; and memory for storing a first value indicative of said reference amplitude resulting from said measuring means, and a second value indicative of said frequency.

* * * * *